United States Patent
Howard, Jr. et al.

(10) Patent No.: US 7,238,263 B2
(45) Date of Patent: Jul. 3, 2007

(54) CORROSION TESTER

(75) Inventors: J. Darby Howard, Jr., Walnut Creek, CA (US); Mohammed Ali, Walnut Creek, CA (US); Chris Lisson, Walnut Creek, CA (US)

(73) Assignee: California Corrosion Concepts, Inc., Walnut Creek, CA (US)

( * ) Notice: Subject to any disclaimer, the term of this patent is extended or adjusted under 35 U.S.C. 154(b) by 256 days.

(21) Appl. No.: 10/955,338

(22) Filed: Sep. 24, 2004

(65) Prior Publication Data

US 2006/0065551 A1    Mar. 30, 2006

(51) Int. Cl.
*C23F 13/00*    (2006.01)

(52) U.S. Cl. .................. 204/196.03; 204/196.05; 204/196.06; 204/196.07; 73/86; 324/71.2

(58) Field of Classification Search ........... 204/196.03, 204/196.05, 196.06, 196.07; 73/86; 324/71.2
See application file for complete search history.

(56) References Cited

U.S. PATENT DOCUMENTS

| | | | |
|---|---|---|---|
| 3,953,742 A | 4/1976 | Anderson et al. | |
| 4,380,763 A * | 4/1983 | Peart et al. | 340/870.16 |
| 5,208,162 A * | 5/1993 | Osborne et al. | 436/6 |
| 5,748,008 A | 5/1998 | Landreth | |
| 5,814,982 A | 9/1998 | Thompson et al. | |
| 5,999,107 A | 12/1999 | Cooper et al. | |
| 6,054,038 A * | 4/2000 | Davis et al. | 205/776.5 |
| 6,183,625 B1 | 2/2001 | Staerzl | |
| 6,265,879 B1 | 7/2001 | Landreth | |
| 6,346,188 B1 | 2/2002 | Shuster et al. | |
| 6,556,027 B2 * | 4/2003 | Banks | 324/700 |
| 6,559,660 B1 | 5/2003 | Staerzl | |
| 6,841,059 B1 * | 1/2005 | Staerzl | 205/727 |
| 2003/0074162 A1 | 4/2003 | Fourie et al. | |

* cited by examiner

*Primary Examiner*—Bruce F. Bell
(74) *Attorney, Agent, or Firm*—Charles L. Thoeming

(57) ABSTRACT

A portable, handheld, automatic protection level interpreting cathodic protection meter for testing the level of protection being afforded to metallic structures protected by either sacrificial anode or impressed current cathodic protection systems, or both. The meter is suitable over a variety of environments including salt water, freshwater, and soil. The operator can select both the type of metal to be tested as well as the type of reference electrode that is being used. The meter automatically calibrates data interpretation of the level of protection based on the operator's selections and eliminates any voltage drop error existing between a reference electrode and the structure being protected.

26 Claims, 5 Drawing Sheets

CORROSION TESTER

CROSS-REFERENCES TO RELATED APPLICATIONS

None.

STATEMENT REGARDING FEDERALLY SPONSORED RESEARCH OR DEVELOPMENT

None.

REFERENCE TO A MICRO-FICHE APPENDIX

None.

BACKGROUND OF THE INVENTION

Field of the Invention

The present invention relates to a portable, handheld, automatic protection level interpreting cathodic protection monitoring device for testing the level of protection being afforded to metallic structures that are protected by either sacrificial anode or impressed current cathodic protection systems or combination of both. The apparatus of the present invention can be used for structures in a variety of environments including, but not limited to, salt water and freshwater applications as well as in soil applications. The present invention allows the operator to select both the type of metal to be tested from a range of metals programmed into the device as well as the type of reference electrode that is being utilized. The present invention automatically calibrates data interpretation of the level of protection based on the operator's selections.

The apparatus of the present invention is simple to use and it ensures that a reliable measurement is made by the operator as it is equipped with built in diagnostics that alert the operator to conditions that could result in erroneous measurements such as improper connections and low voltage power supply conditions. The device can measure the constant DC voltage from a sacrificial anode source or the "off cycle" of a modified waveform generated by specific IR drop free impressed current cathodic protection systems. Measuring the "off cycle" of interrupted impressed current systems eliminates the voltage drop error that exists between the reference electrode and the subject structure being tested as a result of the current flow generated by the cathodic protection system which results in more accurate assessment of protection levels.

No specialized training in corrosion science is necessary to use the apparatus of the present invention since light emitting diode ("LED") displays on the monitoring device provide the operator with interpreted protection level results based on the potential measurements and the type of metal and reference electrode selections made by the operator. A liquid crystal display ("LCD") provides the operator with digital formatting of the same potential measurement for advanced testing such as stray current testing, integrity testing of bonding circuits, and the like.

DESCRIPTION OF THE RELATED ART

A search of the prior art located the following United States patents which are believed to be representative of the present state of the prior art: U.S. Pat. No. 6,559,660 B1, issued May 6, 2003, U.S. Pat. No. 6,556,027 B2, issued Apr. 29, 2003, U.S. Patent Publication No. US2003/0074162 A1, published Apr. 17, 2003, U.S. Pat. No. 6,346,188 B1, issued Feb. 12, 2002, U.S. Pat. No. 6,183,625 B1, issued Feb. 6, 2001, U.S. Pat. No. 5,999,107, issued Dec. 7, 1999, U.S. Pat. No. 5,814,982, issued Sep. 29, 1998, U.S. Pat. No. 5,748,008, issued May 5, 1998, and U.S. Pat. No. 3,953,742, issued Apr. 27, 1976.

High input impedance voltmeters have traditionally been used to check the level of cathodic protection on boats, docks and wharfs and other types of marine structures, as well as for buried pipelines, water storage tanks, water treatment plant structures, and the like. Their use, however, generally requires some training and knowledge of corrosion science to interpret the results.

The art also presents devices permanently mounted on boats to measure and interpolate cathodic protection system performance at selected locations only. These devices are not portable, nor do they provide automatic calibration circuitry to permit selection of either the type of metal being tested or the electrode metal being used, or both.

BRIEF SUMMARY OF THE INVENTION

The purpose of the present invention is to provide an easy to use and transport test meter for determining the overall cathodic protection system performance on boats, steel sea walls, steel pilings, metal boat lifts, and other marine structures comprising various metals, as well as for onshore buried steel pipelines, water storage tanks, and the like. The present invention provides such a corrosion tester for use by persons who are not knowledgeable or trained in corrosion science. Use of the present invention will allow the operator to maintain the subject of testing in an optimal "corrosion free" condition. The present invention will alert the operator to conditions when the test subject is not adequately protected and in need of new anodes or supplemental cathodic protection measures.

The present invention provides a handheld, cathodic protection system monitor which collects and interprets the measurement data and indicates the level of protection being provided on the tested structure through the use of LED's on the front of the meter panel. The apparatus of the present invention is equipped with check status indicator signals to alert the operator to conditions that could result in erroneous measurements such as improper connections and low voltage power supply conditions. In this manner, erroneous readings such as those resulting from low voltage power supply to the meter are prevented.

The present invention further features proprietary circuitry to monitor either a direct current ("DC") or a modified square waveform generated by a specific interrupted impressed current cathodic protection source. The meter captures the measurement of the potential reading during the time period that the current generated by the impressed current cathodic protection system is momentarily interrupted, or "off", also known as the bottom of the trough on the waveform, and uses this measurement in the interpretation of the protection level for the subject structure. This feature eliminates voltage drop, or "IR" drop, error caused by current flowing through the electrolyte between the reference electrode and metal being tested and ensures that a more accurate "IR" error free potential measurement is used for the data interpretation and subsequent data display on the monitor.

The device of the present invention is equipped with a selector switch which allows the operator to select the type of metal being tested including, but not limited to, a range of metals from stainless steels, carbon steel, aluminum, brass, bronze, and the like. Once the operator selects the reference metal to be tested on the monitor, the data interpretation is automatically calibrated to that particular metal and the light emitting diode ("LED") display monitor corresponds to that metal.

The device of the present invention further comprises a selector switch which allows the operator to select the type of reference electrode being used including, but not limited to, silver-silver chloride reference electrode, zinc reference electrode, copper-copper sulfate reference electrode, and the like. Once the operator selects the type of reference electrode, the data interpretation is automatically calibrated to that electrode and the LED/LCD display monitor(s) correspond(s) accordingly. It is the ability of this meter to permit the operator to select the type of reference electrode to be used in the measurement that allows the apparatus of the present invention to be used for metallic structures in a variety of environments including saltwater, freshwater, and soil.

The device of the present invention is equipped with a liquid crystal display ("LCD") screen monitor to display the magnitude of the potential being measured in digital format. The LCD screen monitor displays the DC potential of sacrificial cathodic protection systems and the "IR" drop free potential measurement for select impressed current cathodic protection systems. This feature is designed to aid more knowledgeable operators and will accommodate advanced testing such as stray current testing, integrity testing of the bonding circuits, and the like.

Other features, advantages, and objects of the present invention will become apparent with reference to the following description and accompanying drawings.

DETAILED DESCRIPTION OF THE INVENTION

Figure 1:
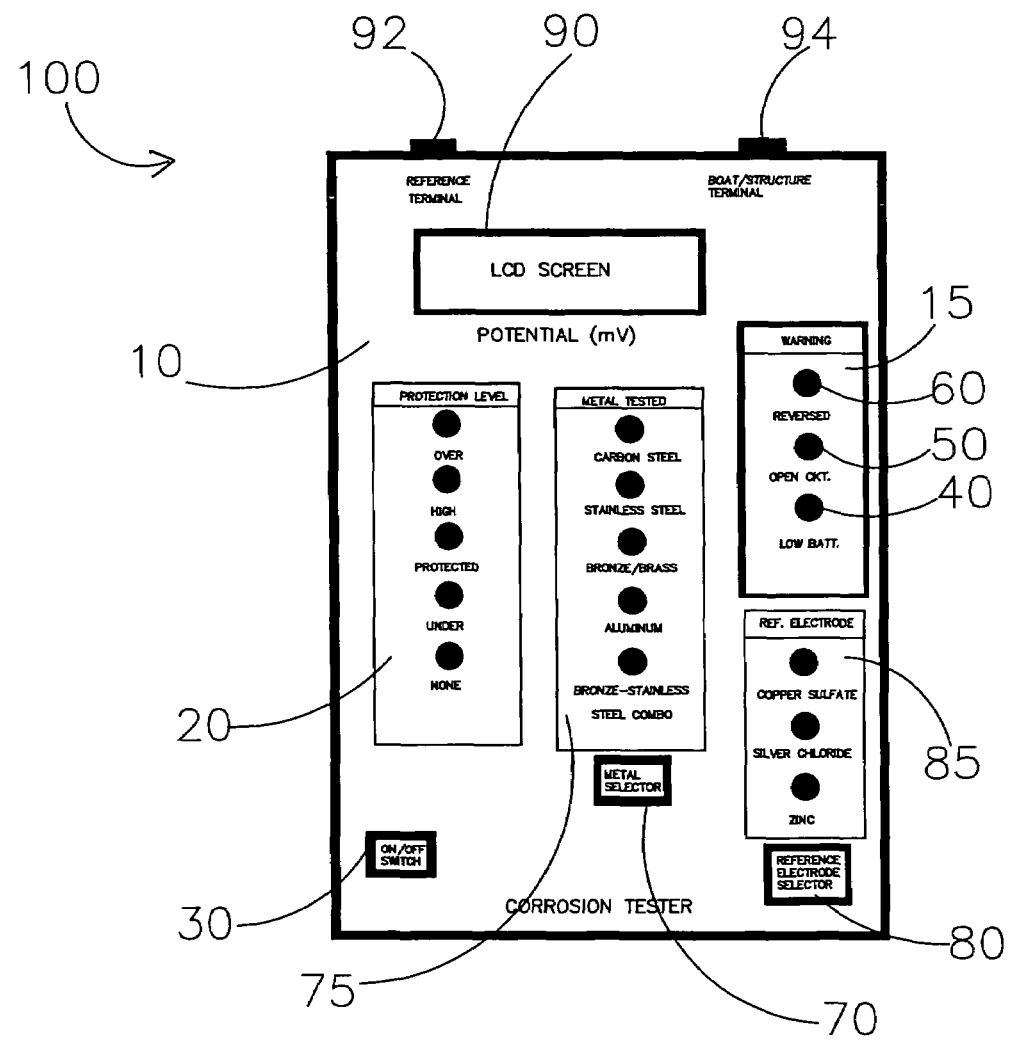
FIG. 1 is a frontal face view of the meter housing of an embodiment of the present invention.

The present invention provides a handheld, cathodic protection system which collects and interprets the measurement data and indicates the level of protection being provided on the tested structure through the use of LED's on the front face of the meter panel. The device of the present invention is equipped with check status indicator signals to alert the operator to conditions that could result in erroneous measurements such as improper connections and low voltage power supply conditions. In this manner, erroneous readings such as those resulting from low voltage power supply to the meter are prevented.

The present invention further features proprietary circuitry to monitor either a DC waveform or a modified square waveform generated by a specific interrupted impressed current cathodic protection source. The meter captures the measurement of the potential reading during the time period that the current generated by the impressed current cathodic protection system is momentarily interrupted, or "off", also known as the bottom of the trough on the waveform, and uses this measurement in the interpretation of the protection level for the subject structure. This feature eliminates voltage drop, or "IR" drop, error caused by current flowing through the electrolyte between the reference electrode and metal being tested and ensures that a more accurate "IR" error free potential measurement is used for the data interpretation and subsequent data display on the monitor.

The device of the present invention is equipped with a selector switch which allows the operator to select the type of metal being tested including, but not limited to, a range of metals from stainless steels, carbon steel, aluminum, brass, bronze, and the like. One the operator selects the reference metal to be tested on the monitor, the data interpretation is automatically calibrated by the proprietary circuitry of the present invention to that particular metal and the monitor LED/LCD display readings correspond accordingly.

The device of the present invention further comprises a selector switch which allows the operator to select the type of reference electrode being used including, but not limited to, silver-silver chloride reference electrode, zinc reference electrode, copper-copper sulfate reference electrode, and the like. Once the operator selects the type of reference electrode, the data interpretation corresponds to the selected metal and the monitor LED/LCD display readings correspond accordingly. It is the ability of this meter to permit the operator to select the type of reference electrode to be used in the measurement that allows the apparatus of the present invention to be used for metallic structures in a variety of environments including saltwater, freshwater, and soil.

The device of the present invention is equipped with a liquid crystal display (LCD) screen to display the magnitude of the potential being measured in digital format. The LCD screen monitor displays the DC potential of sacrificial cathodic protection systems and the "IR" drop free potential measurement for select impressed current cathodic protection systems. This feature of the proprietary circuitry of the present invention is designed to aid more knowledgeable operators and will accommodate advanced testing such as stray current testing, integrity testing of the bonding circuits, and the like.

As depicted in FIG. 1, a preferred embodiment of the present invention for marine corrosion test meter 100 is housed in a four inch by 7 inch by 1.5 inch water-proof box housing 10 made from a high grade plastic. The housing 10 further provides a protection level display panel 20 housing five LED's to indicate the level of cathodic protection achieved on the metal component being tested. These protection levels include, but are not necessarily limited to, over protected 21, high protection 22, protected 23, under protected 24, and no protection or none 25, FIGS. 1 and 3.

Figure 3:
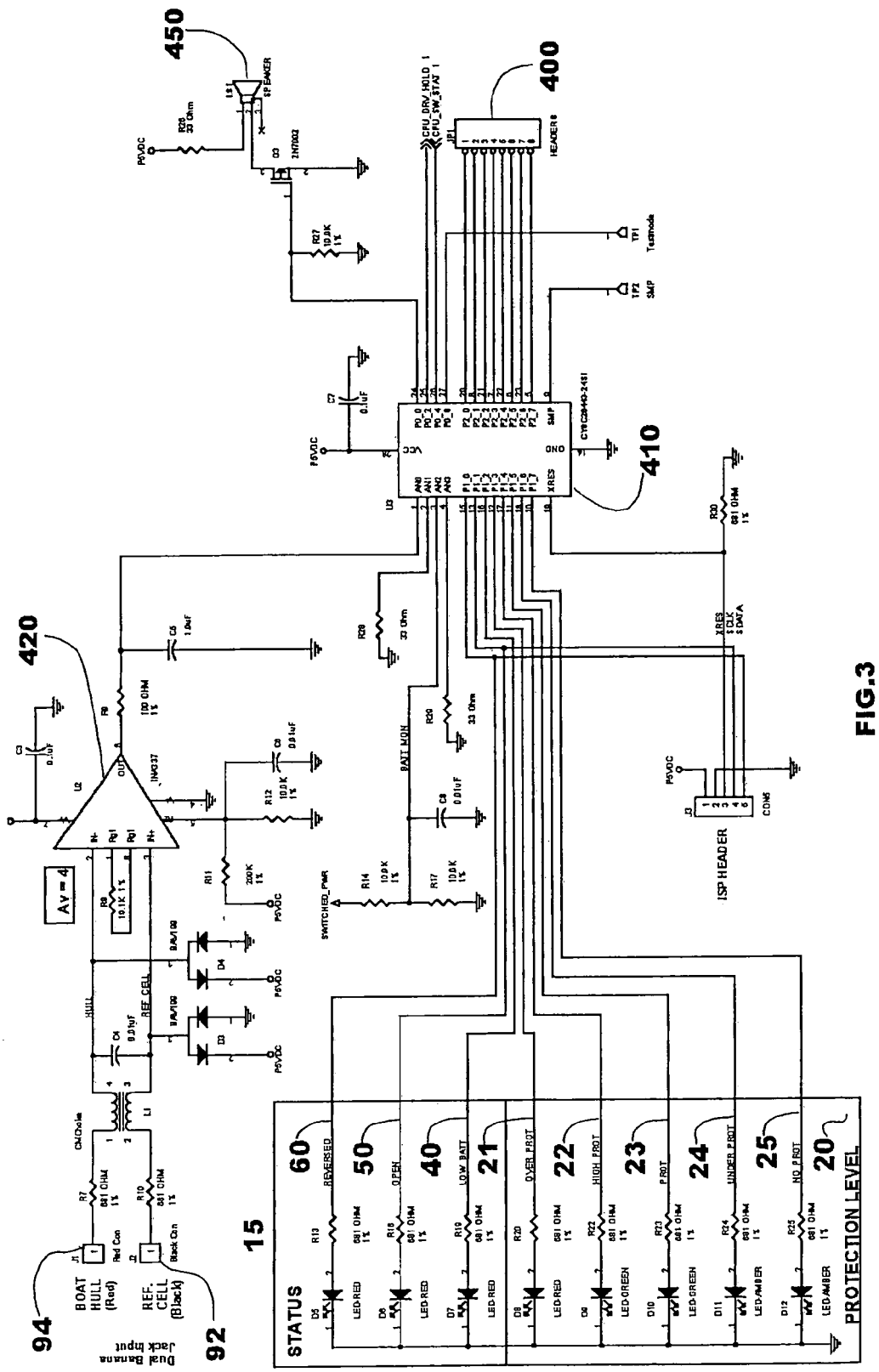
FIG. 3 is an electrical schematic of a portion of a circuit useable in conjunction with embodiments of the present invention.

A system warning display panel 15 provides several light alarms to alert the operator to system failures or possible erroneous readings, FIGS. 1 and 3. On an embodiment of the present invention, one flashing red light emitting diode (LED) 40 is provided within the system warning display panel 15 on the monitor housing as a low battery indicator.

Another red LED 50 is provided within the system warning display panel 15 on the monitor housing as an indicator of a bad structure or reference electrode connection. A third red LED 60 is provided within the system warning display panel 15 on the monitor housing to indicate a reversed polarity connection to the meter.

Figure 5:
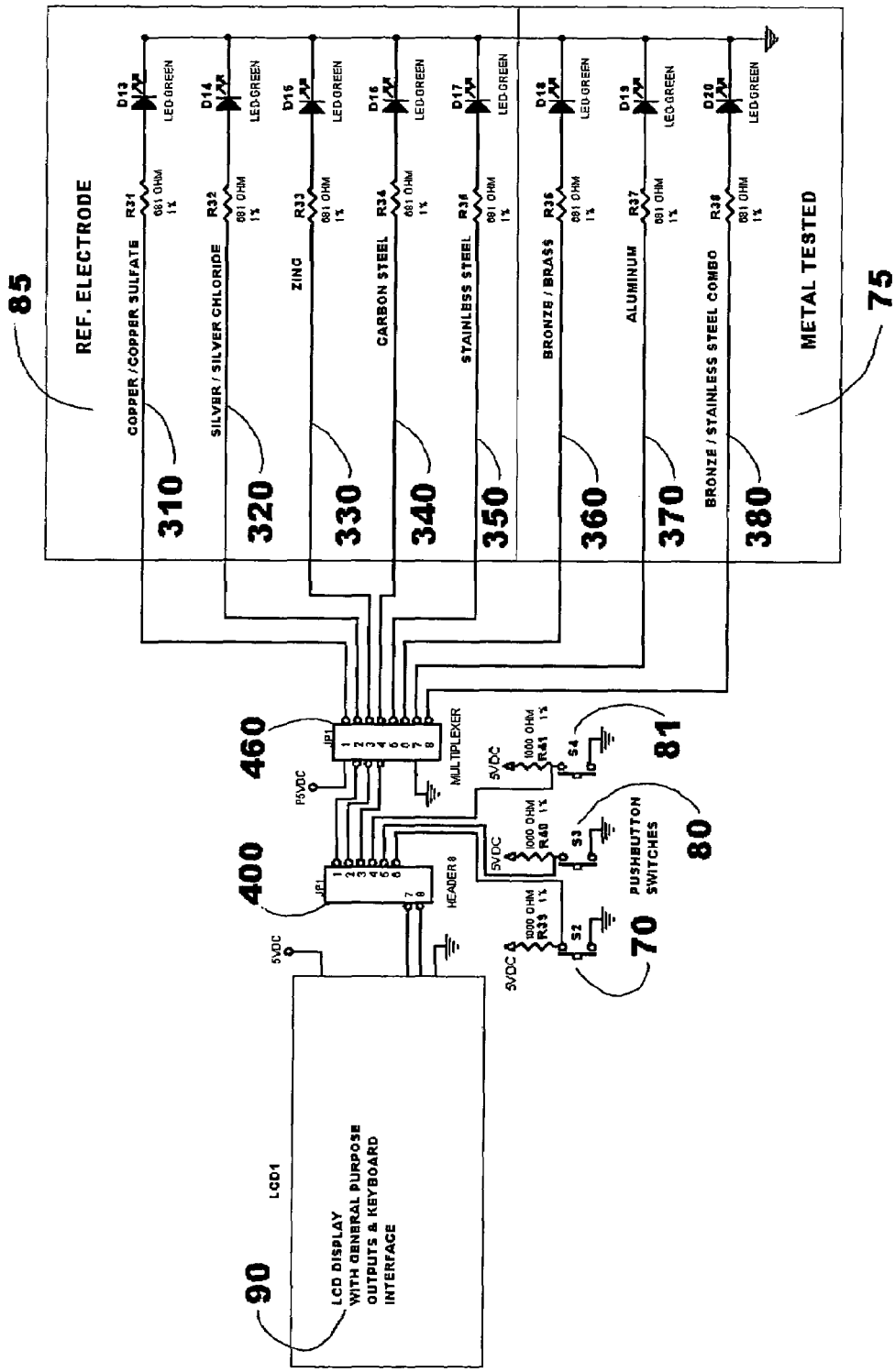
FIG. 5 is a an electrical schematic of a portion of a circuit useable in conjunction with embodiments of the present invention.

As further depicted in FIGS. 1 and 5, a preferred embodiment of the present invention provides a selector switch 70 on the monitor housing box 10 to allow the operator to select the type of metal being tested. The test metal display panel 75 provides indicator lights for a ranges of metals including, but not limited to, carbon steel 340, stainless steel 350, bronze/brass 360, aluminum 370, and bronze-stainless steel combination 380.

Another selector switch 80 is provided on the monitor housing, FIGS. 1 and 5, to select the type of reference electrode being used for testing. The reference electrode display panel 85 provides indicator lights for a ranges of electrodes including, but not limited to, copper sulfate 310, silver chloride 320, and zinc 330. A spare switch, 81, is provided for custom applications as directed by the operator/user of an embodiment of the present invention, FIG. 5.

Figure 4:
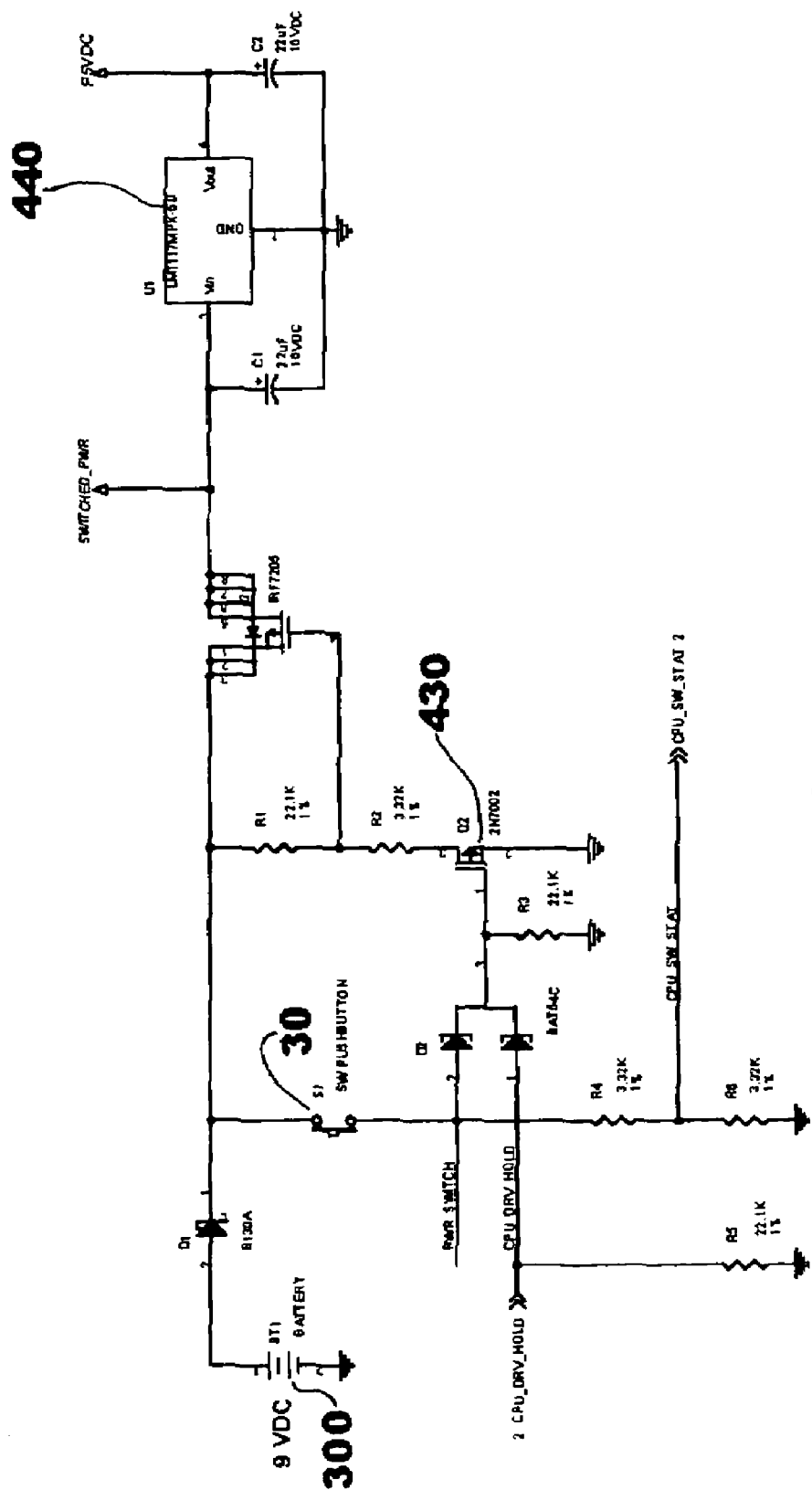
FIG. 4 is an electrical schematic of a portion of a circuit useable in conjunction with embodiments of the present invention.

The monitor device and all enclosed circuitry are powered by a nine volt battery 300, FIG. 4. As such, the preferred embodiment of the present invention provides an easily portable, hand held cathodic protection system monitor. Monitor circuitry, power supply, controls, and output signals are housed in combination within the handheld device to allow easy transportation over a range of locations to check cathodic protection on multiple marine structures or structures in other environments such as freshwater of soil.

As further depicted in FIGS. 1 and 3-5, a preferred embodiment of the present invention provides a flush membrane switch type push button 30 on the monitor box housing 10 to turn on the test meter. To turn on the meter, the operator engages the power switch type push button 30, FIGS. 1, 3, and 4, the power switch goes high until released. The switch state can be observed by the logic level on the central processing unit 410 switch status, CPU_SW_STAT. The central processing unit 410 holds power on by driving the CPU_DRV_HOLD to a logic value "1". The meter will turn off 5 seconds after the power switch type push button 30 was initially activated or when the power switch type push button 30 is released, whichever time period is greater.

As the switch 30 is pressed, power flows to a transistor 430 which in turn powers a 5-volt regulator 440. The 5-volt regulator 440 in turn supplies power to an instrumentation amplifier 420, the microprocessor or central processing unit 410, an annunciator 450, the LCD display 90, and a multiplexer 460. The switch 30 and the microprocessor 410 are connected in parallel to the power transistor 430. The instrumentation amplifier 420 isolates the reference cell 92 and structure lead 94 which are restricted with clamping diodes as well as amplifying the difference between the two. This resulting signal is communicated to the on-board A/D converters within the microprocessor 410. The microprocessor 410 interrogates its on-board data base with the value from the A/D converter in order to determine the level of protection. Once the protection level is determined the microprocessor activates the appropriate LED 20 and/or LCD display 90, if so equipped, to indicate the detected protection level.

Upon startup, the apparatus of the present invention cycles all LED's on the LED display panels, 15, 20, 75 and 85, so the user can detect non-functioning LED's. The apparatus of the present invention is also equipped with a built in annunciator 450 that is used to alert the user to error conditions illuminated on the warning display panel 15. The apparatus of the present invention contains self diagnostics circuits. It can detect the following error conditions: low battery 40, open circuit 50, and reversed leads 60. If the battery 300 level drops to a predetermined level, the unit automatically illuminates the low battery warning LED 40 and the annunciator 450 will start to beep to alert the user to the fact that the meter accuracy may be compromised due to the low battery level. If the test leads, 92 and 94, to the unit are reversed, the reversed polarity LED 60 will illuminate warning the user of the error and the annunciator 450 will produce an audible beeping sound. If an open circuit, from the test leads, 92 and 94, condition exists as a result of a high resistive connection or the like, this device will again illuminate the open circuit warning LED 50 and the annunciator 450 will provide an audible beeping sound.

The unit also contains options for extra buttons in the overlay, 70, 80, and 81, for selecting the type of reference electrode indicated on the display panel 85, and type of metal indicated on the display panel 75 to be tested. When equipped with these buttons, normally there are 3 extra LED's, 360, 370, and 380, for identifying type of reference electrode used, and 5 LED's, 310, 320, 330, 340, and 350, for metal type to be tested. The microprocessor 410 will adjust the indicated level of protection 20 as determined by the selected reference electrode 85 and metal type 75 being tested.

An embodiment of the present invention may also be equipped with a liquid crystal display (LCD) screen 90. The LCD screen 90 can be utilized with or without the LED's. The LCD screen 90 can be programmed to give text descriptions of the protection level 20, battery status 40, open circuit 50 reversed polarity 60, metal tested 75 and reference electrode 85 being utilized. The LCD 90 can provide users with full context menus for selecting metals or commonly utilized combinations of metals in the marine industry, as well as a full range of reference electrodes.

One of the common problems of impressed current cathodic protection systems is the IR drop error between the reference electrode and the structure under protection that exists as a result of the cathodic protection current flowing through the electrolyte. The amount of IR drop error is dependent upon the amount of current flowing through the electrolyte as well as the relative positioning between the reference electrode the anode and the structure. This IR drop error must be taken into account when determining and adjusting the protection level for structures protected with such systems. The professional corrosion industry uses sophisticated current interruption devices and measurement techniques and specially trained corrosion technicians to overcome this problem. These sophisticated testing techniques are not understood or generally available to the recreational boating public and the like. When used with a compatible IR drop free cathodic protection system the apparatus of the present invention is capable of determining and displaying accurate protection levels with the IR Drop error eliminated. This allows the general boating public and the like to more accurately test and adjust the level of protection on their boats or structures easily, even without a rudimentary knowledge of electronics or corrosion engineering principles. This feature further allows the operator to more easily keep the subject structure adequately protected from corrosion, thereby minimizing expensive corrosion related repairs.

The microprocessor 410 samples current flow at a predetermined number of times per second which enables it to determine the off-cycle of a modified square wave which occurs during the interruption cycle of certain IR drop free impressed current cathodic protection systems. The present invention captures this value then uses it in determining the protection level of the structure. This wave form detection feature allows the present invention to detect certain interrupted cycles on impressed current systems which in turn permits 'IR' drop free voltage measurements.

For testing structures that are protected using only galvanic protection, the present invention again provides for easy and accurate assessment of protection levels to the operator. No special training is required to use the present invention and through its use, boat owners and the like will be able to effectively minimize expensive corrosion related repairs. For impressed current systems that are not IR drop free, or have a non-detectable interruption signature, the system of the present invention will display an "On" reading.

The monitor housing box 10 has two input receptacles 92 and 94, FIGS. 1 and 3, one to receive an input jack from a reference terminal 92 and the other to receive an input jack from a marine structure 94. The preferred embodiment of the present invention is equipped with a silver/silver-chloride anode attached to the reference terminal input jack by insulated and shielded wire and an alligator type clamp attached to the marine structure input jack by insulated and shielded wire (not shown). As such, the input 92 originates from an electrode disposed in noncontact association with the structural component to be protected.

Figure 2:
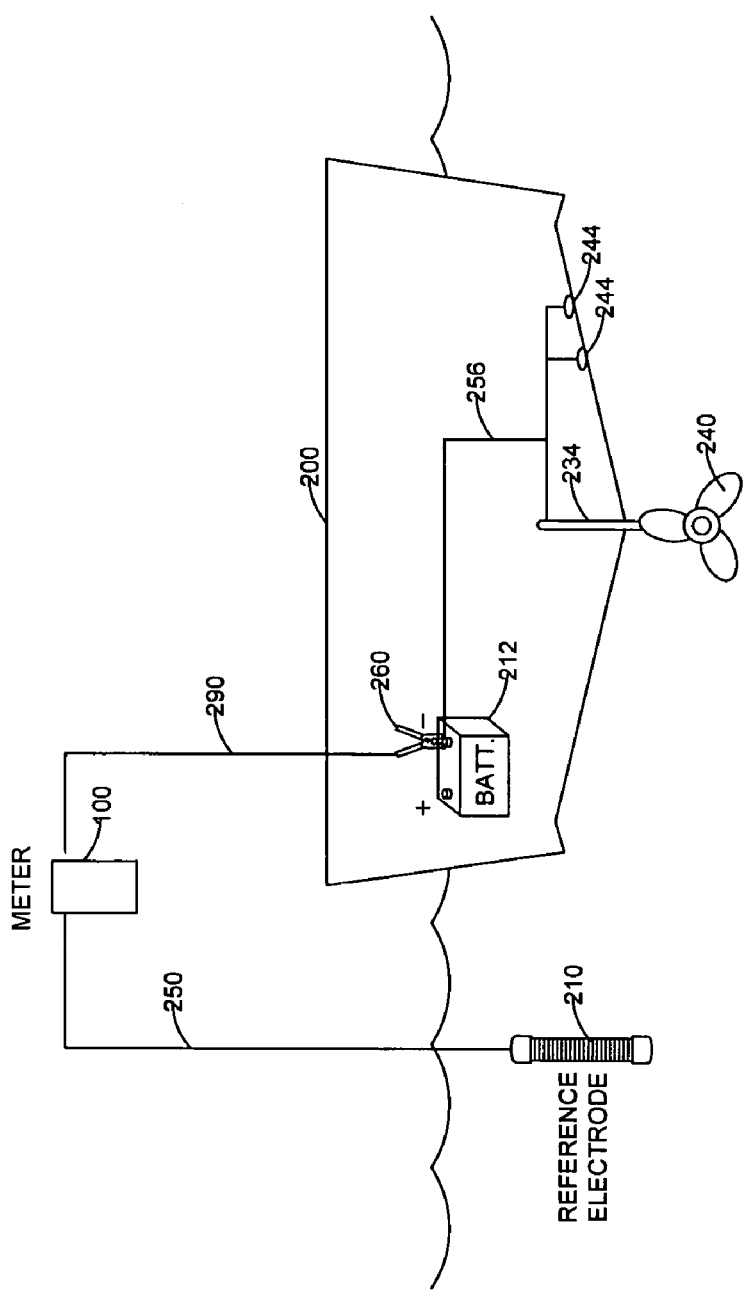
FIG. 2 shows the arrangement of an embodiment of the present invention connected to a cathodic protection circuit of a representative marine vessel.

FIGS. 3-5 are electrical schematics of circuits suitable for performing the functions of the present invention 100. In the following descriptions of FIGS. 3-5, the component values and identification specified refer to one particularly preferred embodiment of the circuits and are not limiting to the present invention. As well understood by those skilled in the art, the absolute magnitudes of the components and the particular types of components used in the circuits of FIGS. 3-5 can be changed without adversely affecting the operation of the present invention as long as certain relationships and characteristics of the components are maintained FIG. 2 depicts use of an embodiment of the apparatus of the present invention to measure the level of cathodic protection on the submerged metallic components of a marine structure, 200, having a stern drive unit 234 with propeller 240. As shown in FIG. 2, the corrosion tester 100 is connected in series to the vessel's battery 212 at the negative post and the reference electrode 210 by lengths of insulated copper wire, 290 and 250, respectively. An alligator type clamp connector 260 secures the length of wire from the tester 10 to the negative battery terminal 212. The marine vessel's stern drive unit 234 is grounded to the metallic thru-hull fittings 244 and connected to the battery 212 by bonding cables 256.

Various embodiments of the foregoing present invention would include, but not be limited to, three switches and the LCD Screen, one switch and the LCD screen, three switches and sixteen LED's, three switches, an LCD screen, and some number of LED's between 1 and 16. Corresponding electrical circuitry for each embodiment would omit unused components from other embodiments.

Accordingly, an improved current tester to monitor a waveform generated by a specific interrupted impressed current cathodic protection source and then measure the potential reading during the time period that the current generated by the impressed current cathodic protection system is momentarily interrupted, or "off", also known as the bottom of the trough on the waveform has been disclosed.

With respect to the above description then, it is to be understood and realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings, circuit schematics, and described in the specification are intended to be encompassed by the present invention.

A latitude of modification, change and substitution is intended in the foregoing disclosure, and in some instances some features of the invention will be employed without a corresponding use of other features. Therefore, it is appropriate that the appended claims be considered broadly and in a manner consistent with the spirit and scope of the invention disclosed herein.

We claim:

1. A meter for marine corrosion testing, comprising:
   means for providing input from a reference electrode disposed in non-contact association with a component to be protected from corrosion;
   means for selecting the type of reference electrode;
   means for automatically calibrating data interpretation based upon the selection of reference electrode;
   means for selecting the type of metal being protected from corrosion;
   means for automatically calibrating data interpretation based upon the selection of the metal being protected;
   means to check proper completeness of electrical circuit between the metal being protected, the electrolyte, and the reference electrode;
   means to check power supply adequacy;
   means to monitor a waveform generated by a specific interrupted impressed current cathodic protection source;
   means to measure the potential of the metal being protected when the current generated by the impressed current cathodic protection source is temporarily interrupted;
   means to provide digital formatted display of magnitude of the potential being measured by the meter;
   means to provide electrical power supply to operate the meter; and
   means to house meter components.

2. The meter of claim 1, wherein means for selecting the type of reference electrode comprises:
   selection means for a plurality of reference electrodes;
   indicator means for the plurality of reference electrodes; and
   means to store a calibrated value for the electrode selected.

3. The meter of claim 2, wherein selection means comprises power switch type push button assembly.

4. The meter of claim 2, wherein indicator means comprises a liquid crystal display type monitor assembly.

5. The meter of claim 2, wherein indicator means comprises a plurality of light emitting diode assemblies.

6. The meter of claim 2, wherein indicator means comprises at least one liquid crystal display type monitor means and a plurality of light emitting diode assemblies.

7. The meter of claim 2, wherein means to store a calibrated value for the electrode selected and means for automatically calibrating data interpretation based upon the selection of reference electrode comprise:
   at least one central processing unit;
   programmable read only memory calibration means comprising values for metal electrodes;
at least one multiplexer; and
at least one micro-processor chip, wherein selection means directs DC voltage to at least one microprocessor chip and at least one multiplexer to indicator means whereby metal electrode calibration and indication correspond to selection.

8. The meter of claim 1, wherein means for selecting the type of metal of the component to be protected from corrosion comprises:
selection means for a plurality of metals;
indicator means for the plurality of metals; and
means to store a calibrated value for the metal selected.

9. The meter of claim 8, wherein selection means comprises power switch type push button assembly.

10. The meter of claim 8, wherein indicator means comprises at least one liquid crystal display type monitor assembly.

11. The meter of claim 8, wherein indicator means comprises a plurality of light emitting diode assemblies.

12. The meter of claim 8, wherein indicator means comprises at least one liquid crystal display type monitor assembly and a plurality of light emitting diode assemblies.

13. The meter of claim 8, wherein means to store a calibrated value for the metal selected and means for automatically calibrating data interpretation based upon the selection of metal comprise:
at least one central processing unit;
programmable read only memory calibration means comprising values for metals;
at least one multiplexer; and
at least one microprocessor chip, wherein selection means directs DC voltage to at least one microprocessor chip and at least one multiplexer to indicator assembly whereby metal calibration and indication correspond to selection.

14. The meter of claim 1, further comprising;
insulated and shielded wire means of predetermined length and two ends;
input plug assembly attached to one wire end;
connection assembly attached to the other wire end; and
input jack assembly on means to house monitor components suitably sized to receive and engage input plug assembly.

15. The meter of claim 1, wherein means for providing input from a reference electrode comprises:
insulated and shielded wire means of predetermined length and two ends;
electrode assembly attached to one wire end;
input plug assembly attached to the other wire end; and
input jack assembly on means to house meter components suitably sized to receive and engage input plug assembly.

16. The meter of claim 1, wherein means to check proper completeness of electrical circuit between the metal being protected, the electrolyte, and the reference electrode comprises:
self-diagnostic circuitry assembly to detect reversed inputs;
self-diagnostic circuitry assembly to detect open circuit; and
indicator assembly.

17. The meter of claim 16, wherein indicator assembly comprises apparatus selected from the group consisting of light emitting diode assembly, liquid crystal display assembly, and annunciator assembly.

18. The meter of claim 1, wherein means to check power supply adequacy comprises:
self-diagnostic circuitry assembly to monitor power supply output; and
indicator assembly.

19. The meter of claim 18, wherein indicator assembly comprises apparatus selected from the group consisting of light emitting diode assembly, liquid crystal display assembly, and annunciator assembly.

20. The meter of claim 1, wherein means to monitor a waveform generated by a specific interrupted impressed current cathodic protection source and means to measure the potential reading during the time period that a current generated by the interrupted impressed current cathodic protection source is off comprise:
at least one microprocessor;
circuitry assembly whereby at least one microprocessor samples voltage at a predetermined rate over time, and wherein the off-cycle of a modified square wave is determined; and
indicator assembly.

21. The meter of claim 20, wherein indicator assembly comprises at least one liquid crystal display assembly.

22. The meter of claim 1, wherein means to provide digital formatted display of magnitude of the potential being measured by the meter comprises:
means to measure and store a potential value from input means;
at least one central processing unit; and
at least one liquid crystal display assembly.

23. The meter of claim 1, wherein means to provide electrical power supply to operate the meter comprises DC power.

24. The meter of claim 1, wherein the reference electrode disposed in common electrolyte association with a component to be protected comprises metals consisting of silver-silver chloride, zinc, copper-copper sulfate, and the like.

25. The meter of claim 1, wherein the component to be protected comprises metals consisting of stainless steels, carbon steel, aluminum, brass, bronze, cooper, and the like.

26. Assembly for testing marine corrosion, the assembly comprising:
an Ag/Ag—Cl reference electrode element attached to one end of a predetermined first length of insulated and shielded wire and an input jack on the other first wire length end;
an alligator clamp with two insulated handles attached to one end of a second predetermined length of insulated and shielded wire and an input jack on the other second wire length end to attach to and provide input from a structure to be monitored;
housing assembly comprising:
two input jack receptors sized to engage and receive the input jacks;
a plurality of protection indicator light emitting diodes;
a plurality of warning indicator light emitting diodes;
at least one test button;
a DC power supply;
at least one central processing unit;
at least one multiplexer; and
at least one microprocessor chip, wherein DC voltage drives at least one microprocessor chip and at least one multiplexer to protection light emitting diodes to provide indication of the level of cathodic protection for the structure to be monitored, DC voltage drives at least one micro-processor chip and at least one multiplexer to warning indicator light emitting diodes to provide indication of reversed inputs, open circuit, or low DC power supply level, and DC voltage drives at least one microprocessor chip and at least one multiplexer to monitor a waveform generated by a specific interrupted impressed current cathodic protection source and to measure the potential reading during the time period that a current generated by the interrupted impressed current cathodic protection source is off.

* * * * *